(12) United States Patent
Carasso et al.

(10) Patent No.: US 9,044,354 B2
(45) Date of Patent: Jun. 2, 2015

(54) FLUID MANAGEMENT DEVICE WITH FLUID TRANSPORT ELEMENT FOR USE WITHIN A BODY

(71) Applicant: McNeil-PPC, Inc., Skillman, NJ (US)

(72) Inventors: Samuel C. Carasso, Milltown, NJ (US); David J. Chase, Somerville, NJ (US); Erin Marsee, Nicholasville, KY (US); Tara Glasgow, Glen Ellyn, IL (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 13/772,544

(22) Filed: Feb. 21, 2013

(65) Prior Publication Data

US 2013/0165892 A1    Jun. 27, 2013

Related U.S. Application Data

(60) Division of application No. 12/396,024, filed on Mar. 2, 2009, which is a continuation of application No. 10/882,913, filed on Jun. 30, 2004, now Pat. No. 7,618,403, which is a continuation-in-part of application No. 10/847,951, filed on May 14, 2004, now Pat. No. 8,247,642.

(51) Int. Cl.
*A61F 13/20* (2006.01)
*A61F 13/511* (2006.01)

(52) U.S. Cl.
CPC ......... *A61F 13/2051* (2013.01); *A61F 13/2031* (2013.01); *A61F 13/2071* (2013.01); *A61F 13/206* (2013.01); *A61F 13/2065* (2013.01); *Y10S 604/904* (2013.01)

(58) Field of Classification Search
CPC ............ A61F 13/2025; A61F 13/2031; A61F 13/2034; A61F 13/2037; A61F 13/2071
USPC .................. 604/378, 385.02, 385.17, 385.18, 604/385.101, 904
See application file for complete search history.

(56) References Cited

U.S. PATENT DOCUMENTS

| | | | |
|---|---|---|---|
| 398,015 | A | 2/1889 | Williams |
| 735,729 | A | 8/1903 | Dowing |
| 867,176 | A | 9/1907 | Warwick |

(Continued)

FOREIGN PATENT DOCUMENTS

| | | | |
|---|---|---|---|
| AU | 748284 | B | 2/2000 |
| CA | 2293599 | A | 6/2001 |

(Continued)

OTHER PUBLICATIONS

U.S. Appl. No. 12/138,009, no official actions received Abandoned, Jun. 12, 2008.

(Continued)

*Primary Examiner* — Melanie Hand
*Assistant Examiner* — Paula L Craig

(57) ABSTRACT

A fluid management device for use in a mammalian body has at least one fluid transport element capable of interfacing with a mammalian body element to provide a substantially uninterrupted fluid conduit. The fluid conduit provides a fluid path between at least one fluid transport element and the storage element. A distal portion of the at least one fluid transport element is capable of extending away from the fluid storage element, and the at least one fluid transport element has a Wing Stiffness of less than about 10 $g_f$.

4 Claims, 14 Drawing Sheets

(56) References Cited

U.S. PATENT DOCUMENTS

| | | |
|---|---|---|
| 1,731,665 A | 10/1929 | Huebsch |
| 1,926,900 A | 9/1933 | Hasse et al. |
| 1,941,717 A | 1/1934 | Rabell |
| 2,099,931 A | 11/1937 | Fourness |
| 2,188,923 A | 2/1940 | Robinson |
| 2,265,636 A | 12/1941 | Eaton |
| 2,301,106 A | 11/1942 | Brown |
| 2,306,406 A | 12/1942 | Robinson |
| 2,328,795 A | 9/1943 | Finks |
| 2,394,219 A | 2/1946 | Vachon |
| 2,412,861 A | 12/1946 | George et al. |
| 2,425,004 A | 8/1947 | Rabell |
| 2,458,685 A | 1/1949 | Crockford |
| 2,464,310 A | 3/1949 | Harwoord |
| 2,613,670 A | 10/1952 | Sokolik |
| 2,624,993 A | 1/1953 | Robertson |
| 2,830,417 A | 4/1958 | Ullman et al. |
| RE24,666 E | 7/1959 | Draghi |
| 3,007,377 A | 11/1961 | Muller |
| 3,055,369 A | 9/1962 | Graham, Jr. |
| 3,058,469 A | 10/1962 | Crockford |
| 3,135,262 A | 6/1964 | Kobler et al. |
| 3,138,159 A | 6/1964 | Schmidt |
| 3,340,874 A | 9/1967 | Burgeni |
| 3,422,496 A | 1/1969 | Wolff |
| 3,431,909 A | 3/1969 | Krusko |
| 3,512,528 A | 5/1970 | Whitehead et al. |
| 3,572,341 A | 3/1971 | Glassman |
| 3,610,243 A | 10/1971 | Jones, Sr. |
| 3,618,605 A | 11/1971 | Glassman |
| 3,643,661 A | 2/1972 | Crockford |
| 3,661,154 A | 5/1972 | Torr |
| 3,706,311 A | 12/1972 | Kokx et al. |
| 3,710,793 A | 1/1973 | Glassman |
| 3,731,687 A | 5/1973 | Glassman |
| 3,732,866 A | 5/1973 | Accavallo |
| 3,762,413 A | 10/1973 | Hanke |
| 3,811,445 A | 5/1974 | Dostal |
| 3,834,389 A | 9/1974 | Dulle |
| 3,845,766 A | 11/1974 | Zoller |
| 3,851,440 A | 12/1974 | Horsky |
| 3,929,135 A | 12/1975 | Thompson |
| RE28,674 E | 1/1976 | Guyette |
| 3,971,378 A | 7/1976 | Krantz |
| 3,983,875 A | 10/1976 | Truman |
| 3,986,511 A | 10/1976 | Olofsson et al. |
| 4,109,354 A | 8/1978 | Ronc |
| 4,211,225 A | 7/1980 | Sibalis |
| 4,212,301 A | 7/1980 | Johnson |
| 4,335,720 A | 6/1982 | Glassman |
| 4,341,214 A | 7/1982 | Fries et al. |
| 4,342,314 A | 8/1982 | Radel et al. |
| 4,351,339 A | 9/1982 | Sneider et al. |
| 4,359,357 A | 11/1982 | Fries et al. |
| 4,372,312 A | 2/1983 | Fendler et al. |
| 4,373,529 A | 2/1983 | Lilaonitkul et al. |
| 4,381,326 A | 4/1983 | Kelly |
| 4,508,256 A | 4/1985 | Radel et al. |
| 4,510,735 A | 4/1985 | Cillario |
| 4,525,983 A | 7/1985 | Libow |
| 4,543,098 A | 9/1985 | Wolfe et al. |
| 4,661,101 A | 4/1987 | Sustmann |
| 4,675,217 A | 6/1987 | Forsman |
| 4,685,178 A | 8/1987 | Nakanishi |
| 4,710,186 A | 12/1987 | DeRossett et al. |
| 4,816,100 A | 3/1989 | Friese |
| 4,863,450 A | 9/1989 | Friese |
| 5,004,467 A | 4/1991 | Hinzmann et al. |
| 5,165,152 A | 11/1992 | Kramer et al. |
| 5,180,620 A | 1/1993 | Mende |
| 5,273,596 A | 12/1993 | Newkirk |
| 5,295,984 A | 3/1994 | Contente et al. |
| 5,387,209 A | 2/1995 | Yamamoto et al. |
| 5,403,300 A | 4/1995 | Howarth |
| 5,458,835 A | 10/1995 | Wilkes et al. |
| 5,498,252 A | 3/1996 | Silber |
| 5,500,270 A | 3/1996 | Langdon et al. |
| 5,536,555 A | 7/1996 | Zelazoski et al. |
| 5,545,155 A | 8/1996 | Hseih et al. |
| 5,567,376 A | 10/1996 | Turi et al. |
| 5,659,934 A | 8/1997 | Jessup et al. |
| 5,688,260 A | 11/1997 | Blanton et al. |
| 5,702,380 A | 12/1997 | Walker |
| 5,759,569 A | 6/1998 | Hird et al. |
| 5,782,063 A | 7/1998 | Boriani et al. |
| 5,802,806 A | 9/1998 | Scaliti |
| 5,817,077 A | 10/1998 | Foley et al. |
| 5,909,884 A | 6/1999 | Schwankhart |
| 5,911,712 A | 6/1999 | Leutwyler et al. |
| 5,928,184 A | 7/1999 | Etheredge et al. |
| 5,928,452 A | 7/1999 | McFall et al. |
| 5,972,505 A | 10/1999 | Phillips et al. |
| 6,177,606 B1 | 1/2001 | Etheredge et al. |
| 6,177,608 B1 | 1/2001 | Weinstrauch |
| 6,183,436 B1 | 2/2001 | Korteweg et al. |
| 6,191,341 B1 | 2/2001 | Shippert |
| 6,206,867 B1 | 3/2001 | Osborn et al. |
| 6,299,573 B1 | 10/2001 | Hull et al. |
| 6,310,269 B1 | 10/2001 | Friese et al. |
| 6,358,235 B1 | 3/2002 | Osborn et al. |
| 6,409,713 B1 | 6/2002 | Osborn et al. |
| 6,433,246 B1 | 8/2002 | Nguyen et al. |
| 6,436,328 B1 | 8/2002 | DiPalma |
| 6,465,713 B1 | 10/2002 | Gell et al. |
| 6,479,130 B1 | 11/2002 | Takai et al. |
| 6,479,728 B1 | 11/2002 | DiPalma |
| 6,554,814 B1 | 4/2003 | Agyapont et al. |
| 6,558,362 B1 | 5/2003 | Chaffringeon |
| 6,570,055 B2 | 5/2003 | Yang et al. |
| 6,595,974 B1 | 7/2003 | Pauley et al. |
| 6,635,800 B2 | 10/2003 | Jackson et al. |
| 6,702,796 B2 | 3/2004 | McFall et al. |
| 6,719,743 B1 | 4/2004 | Wada |
| 6,840,927 B2 | 1/2005 | Hasse et al. |
| 6,860,874 B2 | 3/2005 | Gubernick et al. |
| 7,101,358 B2 | 9/2006 | Domeier et al. |
| 7,112,192 B2 | 9/2006 | Hasse et al. |
| 7,160,279 B2 | 1/2007 | Pauley et al. |
| 7,172,801 B2 | 2/2007 | Hoying et al. |
| 7,179,952 B2 | 2/2007 | Vukos et al. |
| 7,335,194 B2 | 2/2008 | Wada |
| 7,601,415 B2 | 10/2009 | Cree et al. |
| 7,618,403 B2 | 11/2009 | Carasso et al. |
| 8,057,453 B2 | 11/2011 | Chase et al. |
| 8,182,455 B2* | 5/2012 | Carasso et al. ............ 604/385.17 |
| 8,247,642 B2* | 8/2012 | Chase et al. ............... 604/378 |
| 8,353,890 B2 | 1/2013 | Schoelling |
| 8,535,285 B2* | 9/2013 | Chase et al. ............... 604/385.17 |
| 8,604,269 B2* | 12/2013 | Chase et al. ............... 604/378 |
| 8,653,322 B2* | 2/2014 | Chase et al. ............... 604/378 |
| 8,697,936 B2* | 4/2014 | Binner et al. ............... 604/378 |
| 2002/0012373 A1 | 1/2002 | Yokozeki et al. |
| 2002/0026177 A1 | 2/2002 | Lochte et al. |
| 2002/0133135 A1 | 9/2002 | Gell et al. |
| 2002/0138035 A1 | 9/2002 | Hull et al. |
| 2003/0093049 A1 | 5/2003 | Johnson et al. |
| 2003/0097106 A1 | 5/2003 | Hasse et al. |
| 2003/0097108 A1 | 5/2003 | Hasse et al. |
| 2003/0105444 A1 | 6/2003 | Lochte et al. |
| 2003/0135180 A1 | 7/2003 | Nguyen et al. |
| 2003/0149392 A1 | 8/2003 | Arnould |
| 2003/0149416 A1 | 8/2003 | Cole et al. |
| 2003/0208180 A1 | 11/2003 | Fuchs et al. |
| 2003/0229328 A1 | 12/2003 | Costa |
| 2004/0127879 A1 | 7/2004 | Pauley et al. |
| 2004/0147896 A1 | 7/2004 | Mizutani et al. |
| 2005/0049566 A1 | 3/2005 | Vukos et al. |
| 2005/0096620 A1 | 5/2005 | Awolin et al. |
| 2005/0256482 A1 | 11/2005 | Minoguchi et al. |
| 2005/0256484 A1 | 11/2005 | Chase et al. |
| 2005/0256485 A1 | 11/2005 | Carasso et al. |
| 2005/0256486 A1 | 11/2005 | Carasso et al. |
| 2005/0256511 A1 | 11/2005 | Chase et al. |
| 2005/0277904 A1 | 12/2005 | Chase et al. |

(56) References Cited

U.S. PATENT DOCUMENTS

| | | |
|---|---|---|
| 2005/0283128 A1 | 12/2005 | Chase et al. |
| 2006/0004338 A1 | 1/2006 | Torkildsen et al. |
| 2006/0217677 A1 | 9/2006 | Chase et al. |
| 2006/0235361 A1 | 10/2006 | Agyapong et al. |
| 2007/0010388 A1 | 1/2007 | Binner |
| 2007/0049893 A1 | 3/2007 | Binner et al. |
| 2007/0129698 A1 | 6/2007 | Vukos et al. |
| 2007/0282289 A1 | 12/2007 | Glasgow et al. |
| 2008/0255495 A1 | 10/2008 | Danyi et al. |
| 2009/0171310 A1 | 7/2009 | Carasso et al. |
| 2009/0177173 A1 | 7/2009 | Chase et al. |
| 2009/0260205 A1 | 10/2009 | Binner |
| 2010/0069866 A1 | 3/2010 | Binner et al. |
| 2010/0168645 A1 | 7/2010 | Binner et al. |
| 2010/0170069 A1 | 7/2010 | Binner |
| 2010/0192339 A1 | 8/2010 | Binner et al. |
| 2011/0301562 A1 | 12/2011 | Chase et al. |
| 2012/0103529 A1 | 5/2012 | Binner et al. |
| 2012/0109094 A1 | 5/2012 | Binner et al. |
| 2012/0197223 A1 | 8/2012 | Chase et al. |
| 2012/0227228 A1 | 9/2012 | Schoelling |

FOREIGN PATENT DOCUMENTS

| | | | |
|---|---|---|---|
| EP | 1 108 408 A | 6/2001 | |
| GB | 2292526 A | 2/1996 | |
| JP | 48020395 A | 3/1973 | |
| JP | 52020799 U | 2/1977 | |
| JP | 53163894 U | 12/1978 | |
| JP | 56090225 U | 7/1981 | |
| JP | 60171044 A | 9/1985 | |
| JP | 62155835 U | 10/1987 | |
| JP | 3198850 A | 8/1991 | |
| JP | 4120734 U | 10/1992 | |
| JP | 59528 U | 2/1993 | |
| JP | 9510374 T | 10/1997 | |
| JP | 2002508216 T | 3/2002 | |
| JP | 2004508892 T | 3/2004 | |
| WO | WO 83/03537 A | 10/1983 | |
| WO | WO 95/24877 A | 9/1995 | |
| WO | WO 96/00552 A | 1/1996 | |
| WO | WO 97/09017 A | 3/1997 | |
| WO | WO 99/00063 A | 1/1999 | |
| WO | WO 99/00096 A | 1/1999 | |
| WO | WO 99/30659 A | 6/1999 | |
| WO | WO 00/61052 A | 10/2000 | |
| WO | WO 00/63487 A | 10/2000 | |
| WO | WO 01/01906 A | 1/2001 | |
| WO | WO 02/24133 A | 3/2002 | |
| WO | WO 02/058609 A | 8/2002 | |
| WO | WO 02/076357 A | 10/2002 | |
| WO | WO 2005/112856 A | 12/2005 | |

OTHER PUBLICATIONS

U.S. Appl. No. 12/402,867 the Non-final Office Action dated Sep. 10, 2010.
U.S. Appl. No. 12/402,867 the Final Office Action dated Feb. 22, 2011.
U.S. Appl. No. 10/847,952 the Non-final Office Action dated Nov. 25, 2005.
U.S. Appl. No. 10/847,952 the Restriction Requirement dated Aug. 15, 2006.
U.S. Appl. No. 10/847,952 the Final Office Action dated Nov. 26, 2007.
U.S. Appl. No. 10/847,952 the Non-final Office Action dated Jun. 18, 2008.
U.S. Appl. No. 10/847,952 the Final Office Action dated May 29, 2009.
U.S. Appl. No. 10/847,952 the Examiners Answer to Appeal Brief dated Mar. 4, 2010.
U.S. Appl. No. 10/847,952 the BPAI Decision—Examiner Reversed dated Jan. 24, 2012.
U.S. Appl. No. 10/847,952 the Non-Final Office Action dated Feb. 6, 2012.
U.S. Appl. No. 10/847,952 the Notice of Allowance dated May 4, 2012.
U.S. Appl. No. 10/882,913, Patent 7,618,403, the Non-final Office Action dated Nov. 28, 2005.
U.S. Appl. No. 10/882,913, Patent 7,618,403, the Final Office Action dated Dec. 31, 2007.
U.S. Appl. No. 10/882,913, Patent 7,618,403, the Non-final Office Action dated Oct. 29, 2008.
U.S. Appl. No. 10/882,913, Patent 7,618,403, the Notice of Allowance dated May 29, 2009.
U.S. Appl. No. 12/396,024 the Restriction Requirement dated Sep. 21, 2010.
U.S. Appl. No. 12/396,024 the Non-final Office Action dated Jan. 26, 2011.
U.S. Appl. No. 12/396,024 the Final Office Action dated Jul. 21, 2011.
U.S. Appl. No. 10/847,951 the Non-final Office Action dated Nov. 15, 2005.
U.S. Appl. No. 10/847,951 the Restriction Requirement dated Aug. 4, 2006.
U.S. Appl. No. 10/847,951 the Final Office Action dated Nov. 17, 2006.
U.S. Appl. No. 10/847,951 the Advisory Action dated Apr. 17, 2007.
U.S. Appl. No. 10/847,951 the Non-final Office Action dated Jan. 2, 2009.
U.S. Appl. No. 10/847,951 the Final Office Action dated Jul. 7, 2009.
U.S. Appl. No. 10/847,951 the Advisory Action dated Nov. 6, 2009.
U.S. Appl. No. 10/847,951 the Examiners Answer to Appeal Brief dated Mar. 18, 2010.
U.S. Appl. No. 10/847,951 the BPAI Decision-Examiner Affirmed in Part dated Jan. 19, 2012.
U.S. Appl. No. 10/847,951 the Communication dated Apr. 5, 2012.
U.S. Appl. No. 10/847,951 the Notice of Allowance dated May 25, 2012.
U.S. Appl. No. 13/772,524—no office action received yet, Feb. 21, 2013.
U.S. Appl. No. 13/772,544—no office action received yet, Feb. 21, 2013.
U.S. Appl. No. 11/663,137, the Restriction Requirement dated Aug. 2, 2012.
U.S. Appl. No. 11/663,137, the Non-final Office Action dated Oct. 11, 2012.
U.S. Appl. No. 11/663,137, the Final Office Action dated Mar. 6, 2013.
U.S. Appl. No. 11/661,535 the Restriction Requirement dated Jul. 21, 2011.
U.S. Appl. No. 11/661,535 the Non-final Office Action dated Oct. 5, 2011.
U.S. Appl. No. 11/661,535 the Non-final Office Action dated Mar. 2, 2012.
U.S. Appl. No. 11/661,535 the Final Office Action dated Aug. 14, 2012.
U.S. Appl. No. 11/444,792, Patent 7,845,380, the Restriction Requirement dated Jun. 25, 2008.
U.S. Appl. No. 11/444,792, Patent 7,845,380, the Notice of Allowance dated Dec. 4, 2008.
U.S. Appl. No. 11/444,792, Patent 7,845,380, the Notice of Allowance dated Apr. 3, 2009.
U.S. Appl. No. 11/444,792, Patent 7,845,380, the Notice of Allowance dated Dec. 24, 2009.
U.S. Appl. No. 11/444,792, Patent 7,845,380, the Notice of Allowance dated Oct. 1, 2010.
U.S. Appl. No. 11/444,792, Patent 7,845,380, the Notice of Allowance dated Oct. 19, 2010.
U.S. Appl. No. 13/343,272, no office actions received yet, Jan. 4, 2012.
U.S. Appl. No. 13/343,276 the non-final office action dated Mar. 14, 2012, abandoned, Feb. 21, 2013.
U.S. Appl. No. 13/772,922—no office action received yet, Feb. 21, 2013.
U.S. Appl. No. 13/772,949—no office action received yet.

(56) References Cited

OTHER PUBLICATIONS

U.S. Appl. No. 11/478,944, Patent 7,861,494, the Restriction Requirement dated Aug. 1, 2008.
U.S. Appl. No. 11/478,944, Patent 7,861,494, the Notice of Allowance dated Oct. 31, 2008.
U.S. Appl. No. 11/478,944, Patent 7,861,494, the Notice of Allowance dated Feb. 24, 2009.
U.S. Appl. No. 11/478,944, Patent 7,861,494, the Notice of Allowance dated Apr. 30, 2009.
U.S. Appl. No. 11/478,944, Patent 7,861,494, the Notice of Allowance dated Jan. 13, 2010.
U.S. Appl. No. 11/478,944, Patent 7,861,494, the Notice of Allowance dated Nov. 15, 2010.
U.S. Appl. No. 12/722,681, the Non-final Office Action dated Jul. 13, 2012.
U.S. Appl. No. 12/722,681 the Final Rejection dated Jan. 4, 2013.
U.S. Appl. No. 12/722,699 the Non-final Office Action dated Aug. 18, 2011.
U.S. Appl. No. 12/722,699 the Notice of Allowance dated Jan. 17, 2012.
U.S. Appl. No. 12/722,699 the Notice of Allowance dated Jun. 21, 2012.
U.S. Appl. No. 12/724,739, Patent 8.028,500, the Notice of Allowance dated Aug. 9, 2011.
U.S. Appl. No. 10/848,257, the Non-final Office Action dated Nov. 17, 2005 Abandoned.
U.S. Appl. No. 10/848,257, the Restriction Requirement dated Aug. 2, 2006, Abandoned.
U.S. Appl. No. 10/848,257, the Final Office Action dated Nov. 2, 2006 Abandoned.
U.S. Appl. No. 10/848,257, the Non-final Office Action dated Sep. 13, 2007 Abandoned.
U.S. Appl. No. 10/848,257, the Final Office Action dated Aug. 19, 2008 Abandoned.
U.S. Appl. No. 11/762,517, no official actions received Abandoned, Jun. 13, 2007.
U.S. Appl. No. 12/051,562 the Restriction Requirement dated Dec. 31, 2009, Feb. 21, 2013.
U.S. Appl. No. 12/051,562 the Non-final Office Action dated Mar. 29, 2010.
U.S. Appl. No. 12/051,562 the Final Office Action dated Sep. 14, 2010.
U.S. Appl. No. 12/051,562 the Non-Final Rejection dated Jan. 4, 2013.
U.S. Appl. No. 13/772,569—no office action received yet.
U.S. Appl. No. 13/772,585—no office action received yet.
U.S. Appl. No. 11/443,918, Patent 8,057,453, the Restriction Requirement dated Sep. 3, 2008.
U.S. Appl. No. 11/443,918, Patent 8,057,453, the Non-final Office Action dated Apr. 8, 2009.
U.S. Appl. No. 11/443,918, Patent 8,057,453, the Final Office Action dated Oct. 30, 2009.
U.S. Appl. No. 11/443,918, Patent 8,057,453, the Final Office Action dated Mar. 31, 2010.
U.S. Appl. No. 11/443,918, Patent 8,057,453, the Non-final Office Action dated Aug. 16, 2010.
U.S. Appl. No. 11/443,918, Patent 8,057,453, the Final Office Action dated Jan. 26, 2011.
U.S. Appl. No. 11/443,918, Patent 8,057,453, the Notice of Allowance dated Jul. 13, 2011.
U.S. Appl. No. 11/443,918, Patent 8,057,453, the Notice of Allowance dated Sep. 19, 2011.
U.S. Appl. No. 13/212,670, no official actions received yet, Aug. 18, 2011.
U.S. Appl. No. 10/848,208 the Non-final Office Action dated Nov. 8, 2005 Abandoned.
U.S. Appl. No. 11/443,917 the Restriction Requirement dated Sep. 4, 2008.
U.S. Appl. No. 11/443,917 the Non-final Office Action dated Feb. 19, 2009.
U.S. Appl. No. 11/443,917 the Final Office Action dated Nov. 6, 2009.
U.S. Appl. No. 11/443,917 the Non-final Office Action dated Jun. 17, 2010.
U.S. Appl. No. 11/443,917 the Final Office Action dated Dec. 6, 2010.
U.S. Appl. No. 11/443,917 the Non-final Office Action dated Apr. 21, 2011.
U.S. Appl. No. 11/443,917 the Final Office Action dated Oct. 17, 2011.
U.S. Appl. No. 11/443,917 the Notice of Allowance dated Mar. 13, 2012.
U.S. Appl. No. 10/848,347 the Non-final Office Action dated Nov. 8, 2005 Abandoned.
U.S. Appl. No. 11/661,535 the Notice of Allowance dated Apr. 17, 2013.
U.S. Appl. No. 12/051,562 the Final Office Action dated Jun. 26, 2013.
U.S. Appl. No. 13/212,670 the Notice of Allowance dated Jul. 1, 2013.
U.S. Appl. No. 13/444,903 the non-final rejection dated Jul. 25, 2013.
U.S. Appl. No. 13/212,670 the Notice of Allowance dated Aug. 5, 2013.
U.S. Appl. No. 12/402,867 the Notice of Allowance dated Aug. 20, 2013.
U.S. Appl. No. 13/772,569 the Non-Final Rejection dated Sep. 24, 2013.
U.S. Appl. No. 13/772,585 the Non-Final Rejection dated Sep. 9, 2013.
U.S. Appl. No. 12/051,562 the Non-Final Rejection dated Oct. 22, 2013.
U.S. Appl. No. 12/402,867 the Notice of Allowance dated Nov. 6, 2013.
U.S. Appl. No. 12/396,024 the non-final rejection dated Nov. 15, 2013.
U.S. Appl. No. 13/772,524 the non-final rejection dated Nov. 25, 2013.
U.S. Appl. No. 10/847,952 the Notice of Allowance dated Dec. 6, 2013.
U.S. Appl. No. 12/722,681 the Notice of Allowance dated Dec. 13, 2013.
U.S. Appl. No. 13/772,569 the Final Rejection dated Feb. 11, 2014.
U.S. Appl. No. 13/772,585 the Final Rejection dated Feb. 11, 2014.
U.S. Appl. No. 12/722,681 the Notice of Allowance dated Feb. 14, 2014.
U.S. Appl. No. 12/396,024 the Final Rejection dated Apr. 10, 2014.
U.S. Appl. No. 13/772,524 the Final Rejection dated Apr. 10, 2014.
U.S. Appl. No. 11/663,137 the Notice of Allowance dated Aug. 7, 2014.
U.S. Appl. No. 11/663,137 the Notice of Allowance dated Sep. 15, 2014.
U.S. Appl. No. 13/343,272 the Restriction Requirement dated Oct. 2, 2014.
U.S. Appl. No. 13/772,524 the Notice of Allowance dated Jan. 15, 2015.
U.S. Appl. No. 12/396,024 the Notice of Allowance dated Jan. 16, 2015.

* cited by examiner

FLUID MANAGEMENT DEVICE WITH FLUID TRANSPORT ELEMENT FOR USE WITHIN A BODY

CROSS-REFERENCE TO RELATED APPLICATIONS

This invention is a divisional of copending application to Carasso et al., U.S. Ser. No. 12/396,024, entitled "Fluid Management Device with Fluid Transport Element for Use Within a Body", filed Mar. 2, 2009, which is a continuation of application to Carasso et al., U.S. Ser. No. 10/882,913, entitled "Fluid management Device with Fluid Transport Element for Use within a Body", filed Jun. 30, 2004, now U.S. Pat. No. 7,618,403, which is a Continuation-in-Part of application to Chase et al., U.S. Ser. No. 10/847,951, entitled "Fluid Management Device with Fluid Transport Element for use within a Body", filed May 14, 2004, now U.S. Pat. No. 8,247,642, the complete disclosures of which are hereby incorporated herein by reference for all purposes.

This invention is also related to the following copending applications filed on May 14, 2004: "Intravaginal Device with Fluid Acquisition Plates" (U.S. Ser. No. 60/572,054), "Intravaginal Device with Fluid Acquisition Plates and Method of Making" (U.S. Ser. No. 60/572,055), "Method of Using Intravaginal Device with Fluid Transport Plates" (U.S. Ser. No. 10/848,347), "Tampon with Flexible Panels" (U.S. Ser. No. 10/848,257), "Method of Using an Intravaginal Device with Fluid Transport Plates" (U.S. Ser. No. 10/848,208), and "Intravaginal Device with Fluid Acquisition Plates" (U.S. Ser. No. 10/847,952). In addition, this invention is related to "Intravaginal Device with Controlled Expansion" (U.S. Ser. No. 60/584,772, refilled as U.S. Ser. No. 11/172,310), filed on even date herewith, the content of each of which is incorporated herein.

FIELD OF THE INVENTION

The present invention relates to fluid management devices for capturing and storing bodily fluid within the body.

BACKGROUND OF THE INVENTION

Devices for capturing and storing bodily fluid intravaginally are commercially available and known in the literature. Intravaginal tampons are the most common example of such devices. Commercially available tampons are generally compressed cylindrical masses of absorbent fibers that may be over-wrapped with an absorbent or nonabsorbent cover layer.

The tampon is inserted into the human vagina and retained there for a time for the purpose of capturing and storing intravaginal bodily fluids, most commonly menstrual fluid. As intravaginal bodily fluid contacts the tampon, it should be absorbed and retained by the absorbent material of the tampon. After a time, the tampon and its retained fluid is removed and disposed, and if necessary, another tampon is inserted.

A drawback often encountered with commercially available tampons is the tendency toward premature failure, which may be defined as bodily fluid leakage from the vagina while the tampon is in place, and before the tampon is completely saturated with the bodily fluid. The patent art typically describes a problem believed to occur that an unexpanded, compressed tampon is unable to immediately absorb fluid. Therefore, it presumes that premature leakage may occur when bodily fluid contacts a portion of the compressed tampon, and the fluid is not readily absorbed. The bodily fluid may bypass the tampon.

To overcome this problem of premature leakage, extra elements have been incorporated into a basic tampon to try to direct and control the flow of fluid toward the absorbent core.

For example, U.S. Pat. No. 4,212,301 (Johnson) discloses a unitary constructed digital tampon having a lower portion compressed preferably in the radial direction to form a rigid, rod-like element, which provides a central rigidified elongated core and an upper portion left substantially uncompressed. After insertion, the uncompressed portion may be manipulated to contact the vaginal wall to provide an immediate seal against side leakage. The uncompressed portion allows for high absorbent capacity immediately upon insertion. While this tampon may allow for a certain amount of protection from bypass leakage, the uncompressed portion may become saturated before the compressed portion has a chance to expand and become absorbent.

U.S. Pat. No. 6,358,235 (Osborn et al.) discloses a "hollow" bag-like tampon that may have an interior projection made from highly compressed absorbent material. The interior projection is preferably attached to the inside surface of the head of the tampon. The hollow tampon portion may include at least one pleat in the absorbent outer surface and is soft and conformable. The tampon is not pre-compressed to the point where the fibers temporarily "set" and re-expand upon the absorption of fluid. The absorbent portions of the tampon can saturate locally, which leads to bypass leakage.

U.S. Pat. No. 6,177,608 (Weinstrauch) discloses a tampon having nonwoven barrier strips which are outwardly spreadable from the tampon surface to reliably close the free spaces believed to exist within a vaginal cavity. The nonwoven barrier strips extend about the tampon in a circumferential direction at the surface or in a helical configuration about the tampon and purportedly conduct menstrual fluid toward the tampon surface. The nonwoven barrier strips are attached to the cover by means of gluing, heat sealing, needle punching, embossing or the like and form pleats. The nonwoven barrier strips are attached to the tampon blank and the blank is embossed, forming grooves extending in a longitudinal direction. While this tampon purports to direct fluid to the core, it attempts to achieve this by forming pockets of absorbent nonwoven fabric. In order to function, it appears that these pockets would have to be opened during use to allow fluid to enter. However, based upon current understandings of vaginal pressures, it is not understood how the described structure could form such an opened volume.

U.S. Pat. No. 6,206,867 (Osborn) suggests that a desirable tampon has at least a portion of which is dry expanding to cover a significant portion of the vaginal interior immediately upon deployment. To address this desire, it discloses a tampon having a compressed central absorbent core having at least one flexible panel attached along a portion of the side surface of the core. The flexible panel appears to provide the "dry-expanding" function, and it extends outwardly from the core away from the point of attachment. The flexible panel contacts the inner surfaces of the vagina when the tampon is in place and purportedly directs fluid toward the absorbent core. The flexible panel is typically attached to the pledget prior to compression of the pledget to form the absorbent core and remains in an uncompressed state.

U.S. Pat. No. 5,817,077 (Foley et al.) discloses a method of preserving natural moisture of vaginal epithelial tissue while a using a tampon where the tampon has an initial capillary suction pressure at the outer surface of less than about 40 mm Hg. This allows the tampon to absorb vaginal secretions without substantially drying the vaginal epithelial tissue. The multiple cover layers can be used to increase the thickness of the cover material. While this represents a significant advancement in the art, this invention does not address by-pass leakage.

Additionally, U.S. Pat. No. 5,545,155 (Hseih et al.) discloses an external absorbent article that has a set of plates separated by spacer elements. The plates may be treated to affect wettability so that fluid will flow easily across the surface. Extending through the upper plate is a plurality of openings, which allow fluid to flow with little restriction into the space between the upper and lower plates. When the fluid flows downward in the z-direction from the upper plate to the lower plate, it will then flow laterally in the x- and y-directions. Therefore, this external absorbent article can contain fluid gushes, but it does not appear to address the problems relating in particular to intravaginal devices, such as a tampon.

While the prior art is replete with examples of sanitary protection articles that capture bodily fluids both externally and intravaginally, these examples do not overcome the problem of premature failure often identified as by-pass leakage that commonly occurs while using internal sanitary protection devices. Many solutions to this problem have involved increasing the rate of expansion of a highly compressed absorbent article.

Surprisingly, we have found a novel way to address the problem of premature failure. This invention is not dependent on the expansion of the compressed absorbent but rather directing the fluid by the use of inter-plate capillary action. In our invention, we minimize local saturation of the fluid storage element. Our invention also is effective for handling highly viscous menstrual fluid.

SUMMARY OF THE INVENTION

It has been discovered that fluids can be managed in a more effective way by coupling a fluid transport element with a fluid storage element, all held within the body. Several ways to achieve this are disclosed herein.

In one aspect of the invention, a fluid management device for use in a mammalian body has at least one fluid transport element capable of interfacing with a mammalian body element to provide a substantially uninterrupted fluid conduit. The fluid conduit provides a fluid path between at least one fluid transport element and the storage element. A distal portion of the at least one fluid transport element is capable of extending away from the fluid storage element, and the at least one fluid transport element has a Wing Stiffness of less than about 10 $g_f$.

In a further aspect, the invention provides a packaged intravaginal device. The packaged device includes a fluid storage element in fluid communication with a fluid transport element and a packaging element. The fluid storage element has a longitudinal axis and an outer surface. The fluid transport element has at least one flexible plate that is capable of extending radially outward from the fluid storage element and that is bendable about an axis substantially parallel to the longitudinal axis of the fluid storage element, and the fluid transport element has a Wing Stiffness of less than about 10 $g_f$. The packaging element substantially encloses the intravaginal device with at least a portion of a major surface of the flexible plate in contact with at least a portion of the outer surface of the fluid storage element.

Other aspects and features of the present invention will become apparent in those ordinarily skilled in the art upon review of the following description of specific embodiments of the invention in conjunction with the accompanying drawings.

BRIEF DESCRIPTION OF THE DRAWING

FIG. 7a: Side view of alternate embodiment with lateral parallel plates.

FIG. 7b: Transverse cross-section 7a.

FIG. 7c: Transverse cross-section of alternate embodiment with parallel plates formed by cover pleats.

FIG. 7d: Transverse cross-section of alternate embodiment with parallel plates partially extending into storage element.

FIG. 7e: Side view of alternate embodiment with multiple extending parallel plates.

in FIG. 11a.

DETAILED DESCRIPTION OF THE PREFERRED EMBODIMENTS

Figure 1A:
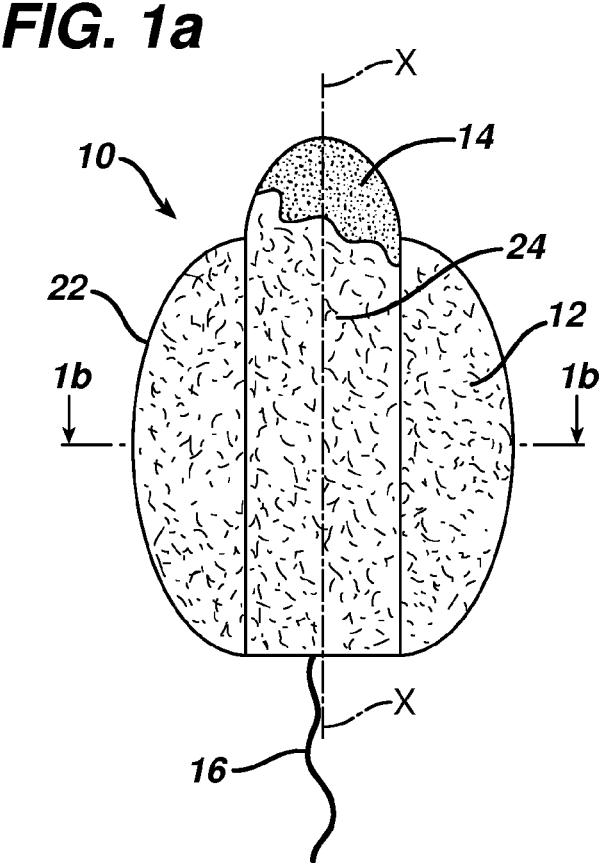
FIG. 1a shows a side elevation of a fluid management device having a pair of fluid transport elements formed as extensions of a cover.

As used herein in the Specification and the Claims, the term "bodily fluid" and variants thereof mean liquids that are produced by, secreted by, emanate from, and/or discharged from a human body.

As used herein in the Specification and the Claims, the term "fluids" and variants thereof relate to liquids, and especially bodily fluids.

As used herein in the Specification and the Claims, the term "sheet" and variants thereof relates to a portion of something that is thin in comparison to its length and breadth.

As used herein in the Specification and the Claims, the term "parallel plate" and variants thereof relates to a system of at least two relatively parallel sheets that are capable of moving fluids through inter-plate capillary action. The individual "plates" in the system may be flexible and/or resilient in order to move within their environment. However, they may be maintained in a substantially facing relationship with relatively constant separation at least in a localized portion of their structure (as compared with their relative length and width. Thus, two sheets could be fluted, but if the flutes are "nested", the sheets would generally remain generally parallel in any given localized portion.

As used herein in the Specification and the Claims, the term "inter-plate capillary action" means the movement of fluid due to a pressure difference across a liquid-air meniscus created within a gap between two substantially parallel plates. The two plates need not be held apart a specific distance, although they should be separable to allow fluid to move between them by inter-plate capillary action. A general equation providing the rise of a fluid between parallel plates is reported as:

$$h = \frac{2\sigma * \cos\theta}{\rho * g * d}$$

in which:
h is rise of fluid between plates
σ is the surface tension of fluid in contact w/plate
θ is contact angle
ρ is density
d is distance between plates, and
g is the gravitational constant Therefore, as long as the contact angle, θ, is less than 90°, there will be some capillary attraction.

As used herein in the Specification and the Claims, the term "porous medium" and variants thereof relates to a connected 3-dimensional solid matrix with a highly ramified network of pores and pore throats in which fluids may flow.

As used herein, the term "separable plates" means any condition of separation of the first plate and the second plate, which allows fluid to move between the plates. This includes situations in which facing surfaces of adjacent first and second plates are touching one another in portions of or across substantially all of their facing surfaces. This also includes situations in which the facing surfaces of the adjacent first and second plates are separably joined together such that upon contact with fluid, the surfaces separate enough to provide for fluid to move between them. This further includes situations in which facing surfaces of adjacent first and second plates are joined together, as long as fluid may still move freely between the surfaces.

As used herein in the Specification and the Claims, the term "in fluid communication" relates to elements that are arranged and configured to allow fluid to move therebetween. The fluid movement may be by interfiber capillary movement, intrafiber capillary movement, osmotic pressure, inter-plate capillary action, mechanical channeling, and the like.

As used herein in the Specification and the Claims, the term "coupled" relates to the relationship between to portions of an integral structure that are either portions of the same material (e.g., two portions of a folded sheet) or are materials that are joined together (e.g., two separate sheets that are bonded together).

As used herein in the Specification and the Claims, the term "fluid management device" and variants thereof include, without limitation, patches for topical or transdermal applications, nasal pads or tampons, diapers, incontinence products, feminine hygiene products (including sanitary napkins and intravaginal devices, such as tampons), body wipes, bedsheets and surgical gowns.

Figure 1B:
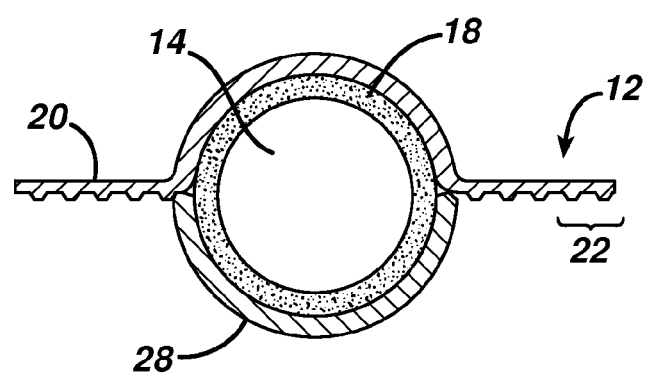
FIG. 1b shows a transverse cross-section of 1a along line 1b-1b.
Figure 2:
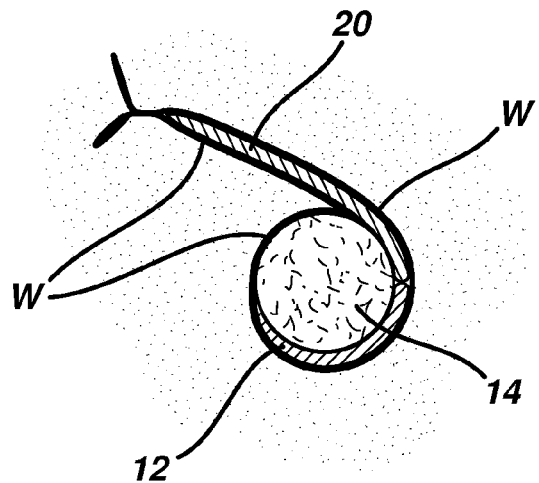
FIG. 2 shows a transverse cross-section of a human vagina with a tampon according to FIG. 1a disposed therein with one fluid transport element extending away from the fluid storage element.

Referring to FIGS. 1a & 1b, one embodiment of this invention provides a fluid management device 10 having at least one fluid transport element 12 in fluid communication with a fluid storage element 14 (FIGS. 1a & 1b show two fluid transport elements 12 located on opposite sides of the fluid storage element 14). The device may also include a withdrawal mechanism, such as a string 16. The device may further include a fluid transfer layer 18 to move collected fluid about the fluid storage element 14. The fluid transport element 12 has at least one plate 20 that has a distal portion 22 that is capable of extending away from the fluid storage element 14. When inserted, the at least one plate 20 can provide two surfaces that can interact with vaginal walls "W" to create two sets of parallel plates as shown in FIG. 2, providing a substantially continuous fluid path to the fluid storage element 14.

As mentioned above, the fluid management device 10 of the present invention may include a transfer or distribution layer 18. The transfer layer or distribution layer 18, if present, is generally positioned as an outer layer of the fluid storage element 14, although it may in turn be enclosed by a cover 24, and the transfer layer usually directly contacts the fluid storage element. If included, the transfer layer may be made of any known material that will take up fluid and then distribute and release it to an adjacent absorbent layer for storage. Transfer layers have a relatively open structure that allows for movement of fluid within the layer. Suitable materials for such transfer layers include fibrous webs, resilient foams, and the like.

The transfer layer provides a means of receiving bodily fluid from the fluid transport element and holding it until the fluid storage element has an opportunity to receive the fluid. The transfer layer is, preferably, more dense than the cover layer and has a larger proportion of smaller pores than does the cover layer. These attributes allow the transfer layer to contain bodily fluid and hold it away from the outer side of the cover layer, thereby preventing the fluid from re-wetting the cover layer and its outer surface. However, the transfer layer is preferably not so dense as to prevent the passage of the fluid through the transfer layer and into the underlying fluid storage element.

The transfer layer may include various materials, including, for example, fibrous webs, resilient foams, and the like. The transfer layer may include cellulose fibers such as from wood pulp, single component or bicomponent fibers that include thermoplastic materials (such as, polyester, polypropylene, polyethylene, among others) in fiber or other forms, rayon, organic binders (such as, copolymers of vinyl, acrylic and/or other monomers that may be coated onto thermoplastic fibers or otherwise incorporated into the transfer layer) among other materials known to the art. The transfer layer may, for example, have a basis weight in a range from about 40 gsm to about 120 gsm, a thickness in a range from about 0.5 mm to about 4 mm, a density in a range from about 0.03 g/cc to about 0.15 g/cc.

The mass of materials making up the transfer layer may be absorbent, even if the materials themselves are not absorbent. Thus, transfer layers that are made of hydrophobic, nonabsorbent fibers may be able to accept large volumes of fluid into interfiber void spaces while the fibers themselves do not absorb any significant quantities of fluid. Likewise, open-celled foam structures that are made from nonabsorbent materials may also absorb fluid into the cells of the foam. The walls of the cells, however, do not absorb any fluid. The cumulative spaces within the transfer layer, i.e., the interfiber void spaces in the fibrous transfer layer or the open cells in the foam transfer layer, function much like a container to hold fluid.

Typically, transfer layer fibrous webs are made of resilient, nonabsorbent materials to provide void volume and to allow for free movement of fluid through the structure. Transfer layers that are made from webs of mostly absorbent fibers absorb the fluid as it enters the structure and do not distribute it throughout the rest of the structure as efficiently as webs containing non-absorbent materials. Transfer layer fibrous webs that include nonabsorbent materials are expected to provide void volume and to allow for more free movement of fluid through the structure. Examples of such materials include polypropylene, polyethylene, polyester, bicomponent materials, nylon and mixtures or combinations thereof. Alternative materials for transfer layers include apertured film; it can be any other nonwoven material, such as, foam or netting, which transports fluid and in combination with the cover, may provide masking of the fluid storage element.

Figure 3A:
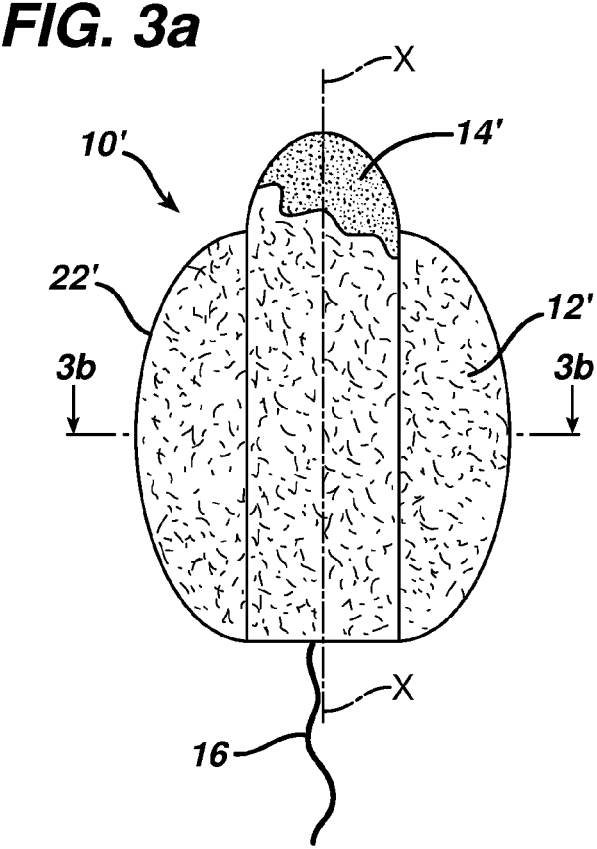
FIG. 3a shows a side elevation of an alternate fluid management device having a pair of fluid transport elements formed as extensions of a cover.
Figure 3B:
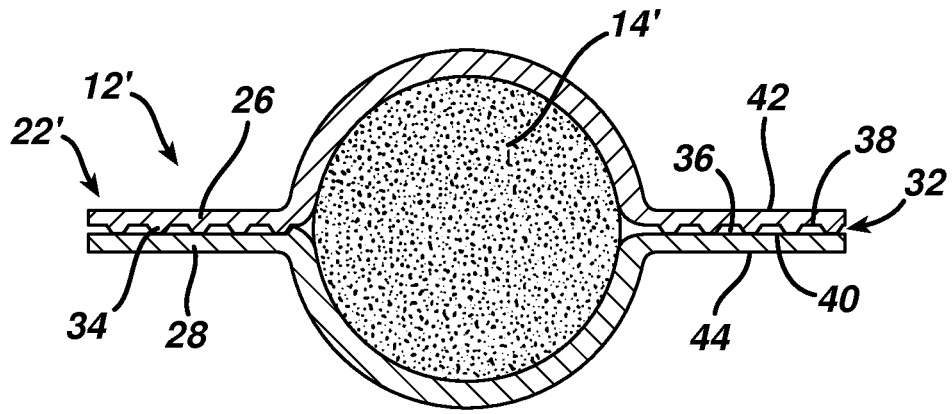
FIG. 3b shows a transverse cross-section of the device in 3a along line 3b-3b.
Figure 3C:
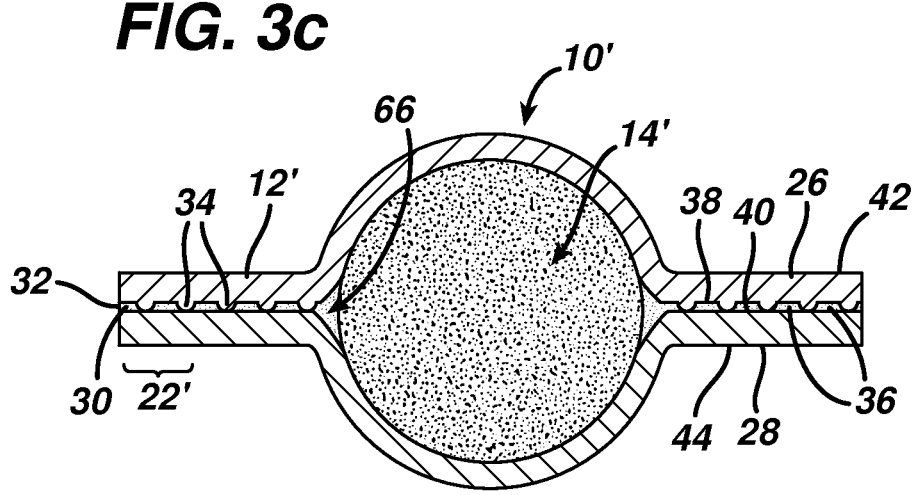
FIG. 3c shows the transverse cross-section shown in 3b, after the introduction of a fluid between the plates of the fluid transport element.
Figure 5A:
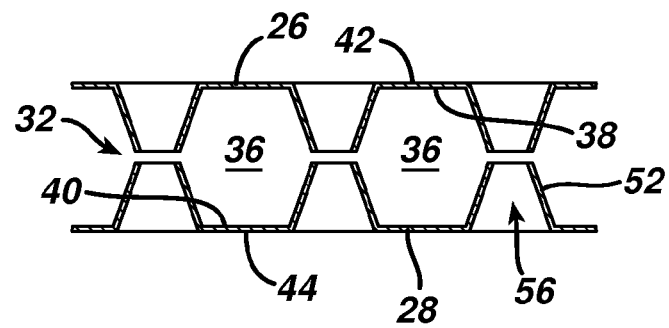
FIG. 5a-c show enlarged cross-sections of alternate embodiments of fluid transport elements of the present invention formed of polymeric apertured formed film having differing orientations of the formed film plates.
Figure 5B:
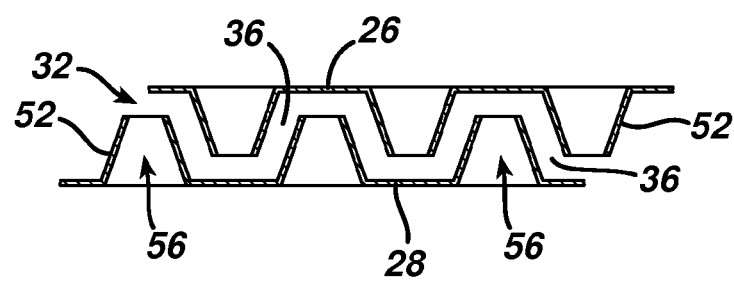
Figure 5C:
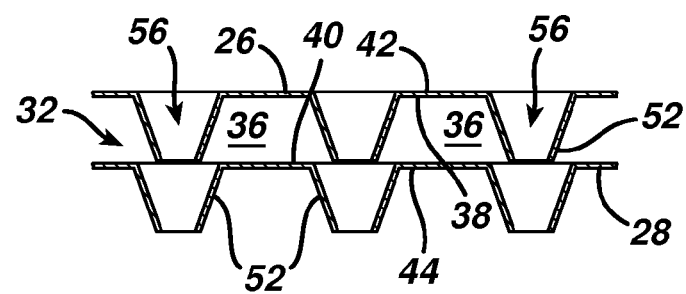

A further alternate embodiment is shown in FIGS. 3a-3c in which an intravaginal device 10' has at least one fluid transport element 12' in fluid communication with a fluid storage element 14' (FIGS. 5a-5c show two fluid transport elements 12' located on opposite sides of the fluid storage element 14'). The device may also include a withdrawal mechanism, such as a string 16. The fluid transport element has at least a first plate 26 and a second plate 28. The first and second plates combine to provide a set of parallel plates, and the fluid transport elements 12' are shown as extending radially away from the fluid storage element 14'. Additional plates may also be incorporated into each fluid transport element 12'.

The plates are arranged and configured to allow the introduction of bodily fluid 30 to separate a plate from adjacent plate(s) (FIG. 3c). At least one opening 32 allows the introduction of bodily fluids 30. Optionally, one or more spacer elements 34 can be inserted to establish and to maintain space between adjacent plates.

FIG. 3b shows a pair of parallel plates prior to the introduction of a fluid. In this view, the facing surfaces of the adjacent plates 26, 28 are in contact. On the other hand, FIG. 3c shows the set of parallel plates separated by a bodily fluid 30, providing an inter-plate capillary gap 36 between the inwardly oriented surface 38 of the first plate 26 and the first surface 40 of the second plate 28. This inter-plate capillary gap 36 is sufficient to provide inter-plate capillary action to allow the fluid transport element 12' to acquire, to spread, and to move bodily fluids 30 from the vagina to the fluid storage element 14'. The first plate 26 also has an outwardly oriented surface 42, and the second plate 28 also has an opposite surface 44.

In each of these embodiments, a distal portion 22' of the fluid transport element 12' is capable of extending away from the fluid storage element 14' and thereby creating a substantially uninterrupted fluid conduit from a fluid source to the fluid storage element.

The plates 26, 28 can be made of almost any hydrophobic or hydrophilic material, preferably sheet-like. The thickness of each plate is not critical. However, it can preferably be selected from the range of from about 0.005 to about 0.050 inch. The materials of construction and the thickness of the plates should be designed so that they are sufficiently stiff and/or resistant to wet collapse when exposed to fluid. Such materials provide a fluid transport element 12' that is strong enough to prevent rupturing during handling, insertion, and removal and to withstand vaginal pressures during use.

Figure 4A:
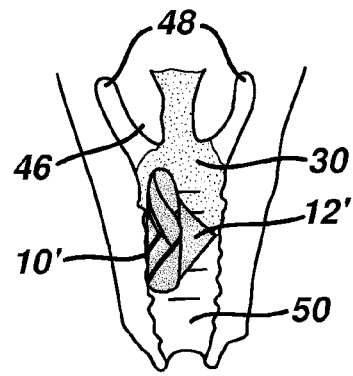
FIGS. 4a-c show a series of coronal cross-sectional views of an intravaginal device according to the present invention during stages of fluid discharge and absorption.
Figure 4B:
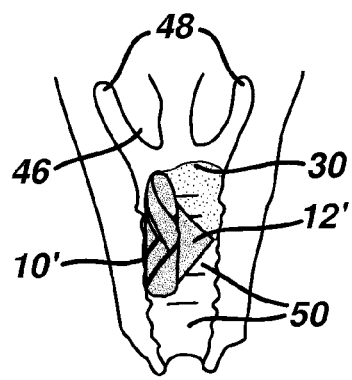
Figure 4C:
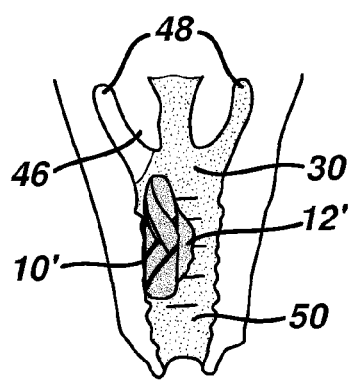

In greater detail, FIGS. 4a-c depict a tampon according to the present invention disposed within a user's vagina with one fluid transport element 12' extending across the flattened vagina. In FIG. 4a, the menstrual fluid 30 flows from the cervix 46 into the fornix 48 and vagina 50 above the intravaginal device (e.g., tampon 10'). The extended fluid transport element 12' disrupts the free flow of menstrual fluid 30 along the full length of the vagina 50. In FIG. 4b, the fluid transport element 12' has sufficient stiffness to remain extended during the tampon's absorption of menstrual fluid and to provide a substantially continuous fluid path to the fluid storage element 14.

In contrast, FIG. 4c shows a fluid transport element 12' that lacks sufficient stiffness and that has collapsed under the pressure of the menstrual fluid 30. This provides a substantially direct path for a significant amount of menstrual fluid 30 to bypass the tampon.

Useful fluid transport elements 12' in the form of one or more plate(s) (also described as "wings") should have a "Wing Stiffness" (as defined below in the Examples) of less than 10 grams force ("$g_f$"). Preferably, the Wing Stiffness is about 0.4 $g_f$ to about 4 $g_f$, more preferably about 0.5 $g_f$ to about 3 $g_f$, and most preferably, about 0.5 $g_f$ to about 2 $g_f$.

In particular, materials useful for forming the fluid transport element may have properties such as thermobondability to provide means to incorporate it into the fluid management device. A representative, non-limiting list of useful materials includes polyolefins, such as polypropylene and polyethylene; polyolefin copolymers, such as ethylenevinyl acetate ("EVA"), ethylene-propylene, ethyleneacrylates, and ethylene-acrylic acid and salts thereof; halogenated polymers; polyesters and polyester copolymers; polyamides and polyamide copolymers; polyurethanes and polyurethane copolymers; polystyrenes and polystyrene copolymers; and the like. The fluid transport element may also be micro-embossed or apertured. Examples of films having apertures include for example, three-dimensional apertured films, as disclosed in Thompson, U.S. Pat. No. 3,929,135, and Turi et al, U.S. Pat. No. 5,567,376, as well as two-dimensional reticulated film, such as that described in Kelly, U.S. Pat. No. 4,381,326. FIGS. 5a-c illustrate three combinations of the apertured film of Thompson.

It may be helpful to keep the exposed surface of the fluid transport element as smooth as possible. It may also be helpful to provide it with a low coefficient of friction. These characteristics may provide at least two benefits: (1) the force required to insert the intravaginal device is reduced, and (2) it reduces the damage otherwise caused by scraping of soft, tender vaginal tissue during insertion, wearing and removal.

Plates 26 and 28 may be made from the same material or alternately, plate 26 may be made from a different material than plate 28.

The parallel plates can have any physical structure to provide a resistance to fluid flow vector in the direction parallel to the inwardly oriented surface 38 of the first plate 26 and the first surface 40 of the second plate 28 that is less than the resistance to fluid flow vector in the direction perpendicular to the plates. Preferably, the plates are made from any relatively smooth material. Suitable materials include, without limitation, foil, waxed sheets, film, apertured film, and the like. For example fibrous or porous sheets may be coated with a substantially continuous coating to provide a film- or foil-like surface. Each plate does not need to be made of the same material as its corresponding parallel plate. For instance the first plate 26 could be an apertured film to allow fluid to enter and the second plate 28 could be a solid film to move fluid to the storage element. Of course, the parallel plates must be able to transport fluid between the two layers.

It is preferable that the surface of at least one of the plates of the fluid transport element 12' be sufficiently wettable by the bodily fluids that the intravaginal device 10 is intended to collect (this results largely from a correlation of the surface energy of the plate surface and the bodily fluid(s)). Thus, the bodily fluid will easily wet the plate, and capillarity between the plates will draw these bodily fluids from a source to a fluid storage element that is in fluid communication with the fluid transport element.

Surface treatments can be used to modify the surface energy of the plates 26, 28. In a preferred embodiment a surfactant is applied to increase the wettability of the outer or inner surfaces of at least one plate. This will increase the rate at which the bodily fluids are drawn to and spread by plates, either between two plates or between a plate and the vaginal wall. The surfactant can be applied uniformly to either the inner or outer surfaces or it could be applied with varying coating weights in different regions.

A useful measure to determine the wettability of a plate surface is its contact angle with 1.0% saline. Preferably, the contact angle with 1.0% saline is less than about 90 degrees.

In order to accomplish this, the materials of plates can be chosen from those materials that are known in the art to have low energy surfaces. It is also possible and useful to coat materials that have high-energy surfaces with a surface additive, such as a non-ionic surfactant (e.g., ethoxylates), a diol, or mixtures thereof, in order to increase their wettability by bodily fluids. Such additives are well known in the art, and examples include those described in Yang et al., U.S. App. No. 2002-0123731-A1, and U.S. Pat. No. 6,570,055. Other means of increasing wettability can also be used, such as by corona discharge treatment of, for example, polyethylene or polypropylene, or by caustic etching of, for example, polyester.

The surfaces of the first and second plates facing each other can have a variety of surface textures, ranging from smooth to highly textured. The texturing element may be included as a spacer 34.

The desire to include spacers 34 or texture may be based on the material's ability to withstand wet collapse when simultaneously subjected to compressive forces and fluid.

The spacer elements 34 can be separate elements applied to one or more of the plates, or they can be integral portions of a plate that extend away from one of the plate's major surfaces. A representative list of such separate spacer elements includes, without limitation, foamed materials such as polystyrene foam; particles such as beads and crystals; discontinuous material such as netting, thread, wax, adhesive, any discrete element that causes a separation between the plates and the like.

Integral spacer elements 34 can be thickened portions of the plate material or deformations of the plate material. A representative list of such an integral spacer element includes, without limitation, nubbles, embossments, corrugations, deformations, and the like. Included in this definition are surface treatments that permanently bond a secondary material to a surface of a first. One example of a deformation is provided as the sidewalls 52 of a "three-dimensional" polymeric apertured formed film material shown in FIGS. 5a-c. FIG. 5a shows the sidewalls 52 of inwardly facing surface 38 and the first surface 40 of the second plate 28 in facing relationship. FIG. 5b shows a second arrangement of the apertured film plates where the sidewalls 52 are nested. FIG. 5c illustrates a third configuration of the apertured film plates where the sidewalls 52 are on the inwardly facing surface 38 of the first plate 26, and sidewalls 52 are on the opposite surface 44 of the second plate 28.

Figure 6:
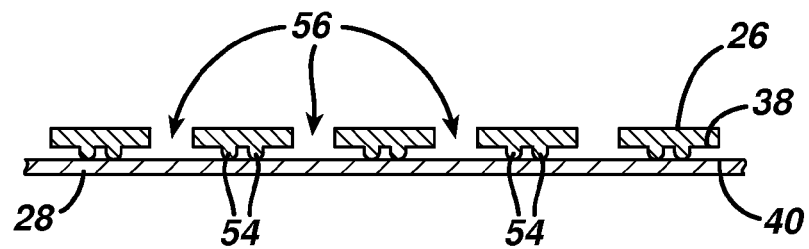
FIG. 6 shows an enlarged cross-section of an alternate embodiment of a fluid transport element of the present invention having nubbles to separate a set of film plates.

In another example, shown in FIG. 6, the spacer elements are nubbles 54 extending from the inward surface 38 of the first plate 26 and resting on the first surface 40 of the second plate 28.

In order to maintain stability against sliding of the plates with respect to each other and changing of the space between them, it is acceptable, and may be preferable, to secure some local areas of contact between the spacer elements 34 and the adjacent plate or even between spacer elements 34 of two adjacent plates. The plates may be secured through means known to those of ordinary skill in the art. A representative list of such securing means includes, without limitation, thermobonding, adhering, crimping, embossing, ultrasonic bonding or welding, and the like. The adhesive may be applied between the spacer elements and the first and second plates. Preferably, the adhesive is wettable.

The at least one opening 32 can be at the edge of the plates, e.g., edges of adjacent plates are separated or plates themselves may have at least one opening. The openings need not be uniform. For example, one opening 32 may be located at the edge of the plates and a plurality of smaller openings or apertures 56 can be distributed throughout one or more plate. Preferably, each plate has a plurality of openings distributed throughout. An example of openings distributed throughout is an apertured film. The distribution can be uniform or arranged to provide regions of higher open area and regions of lower open area.

A plurality of openings or apertures 56 may extend through at least one of the first and second plates 26, 28. These apertures 56 may extend completely through the plate and may be present in both of the plates. The apertures 56 allow fluid that contacts the outward surface 42 of the first plate 26 or the opposite surface 44 of the second plate 28 to flow into the inter-plate capillary gap 36 between the plates with as little restriction as possible. In the example of apertured film, it is preferred that the total surface area of the plate occupied by the openings is from about 5% to preferably about 50%. More preferably, it will be from about 25% to about 45%. Having this much open area formed in a plate will allow fluid that is deposited on that plate to easily flow into the inter-plate capillary gap 36.

It is preferable that any individual opening 32, 56 is large enough to easily pass any highly viscous material, including menstrual fluid. While the geometry of the openings is not critical, the opening 32, 56 should be sized sufficient to allow easy passage of non-absorbable material. If the apertures 56 are not circular, then the measurement should be made across the narrowest part of the opening, which would be most restrictive to the flow of non-absorbable material.

In the example of unapertured film that has an opening 32 at the ends of the plates 26, 28, the size of the opening 32 is a result of the fluid's ability to separate the plates.

It is preferred that the apertures 56 are large enough to let viscous fluid pass through but not too large to create too rough of a surface as to compromise the wearer's comfort. A preferred aperture 56 is circular and is between 10 mils and 40 mils in diameter. Most preferably it is between 18 mils and 27 mils.

Open area may be determined by using image analysis to measure the relative percentages of apertured and unapertured, or land, areas. Essentially image analysis converts an optical image from a light microscope into an electronic signal suitable for processing. An electronic beam scans the image, line-by-line. As each line is scanned, an output signal changes according to illumination. White areas produce a relatively high voltage and black areas a relatively low voltage. An image of the apertured formed film is produced and, in that image, the holes are white, while the solid areas of thermoplastic material are at various levels of gray. The more dense the solid area, the darker the gray area produced. Each line of the image that is measured is divided into sampling points or pixels. The following equipment can be used to carry out the analysis described above: a Quantimet Q520 Image Analyzer (with v. 5.02B software and Grey Store Option), sold by LEICA/Cambridge Instruments Ltd., in conjunction with an Olympus SZH Microscope with a transmitted light base, a plan 1.0.times. objective, and a 2.50× eyepiece. The image can be produced with a DAGE MTI CCD72 video camera.

A representative piece of each material to be analyzed is placed on the microscope stage and sharply imaged on the video screen at a microscope zoom setting of 10×. The open area is determined from field measurements of representative areas. The Quantimet program output reports mean value and standard deviation for each sample.

Referring to FIGS. 7a-13, the first and second plates 26, 28 may be separate elements (i.e, adjacent to each other but not necessarily joined) or they may be extensions of the same sheet-like material, e.g., formed by a fold in a sheet of material (as shown in FIGS. 7a-7e). In such a folded embodiment, the material is folded to form a pleat with the first and second plates facing each other.

Figure 7A:
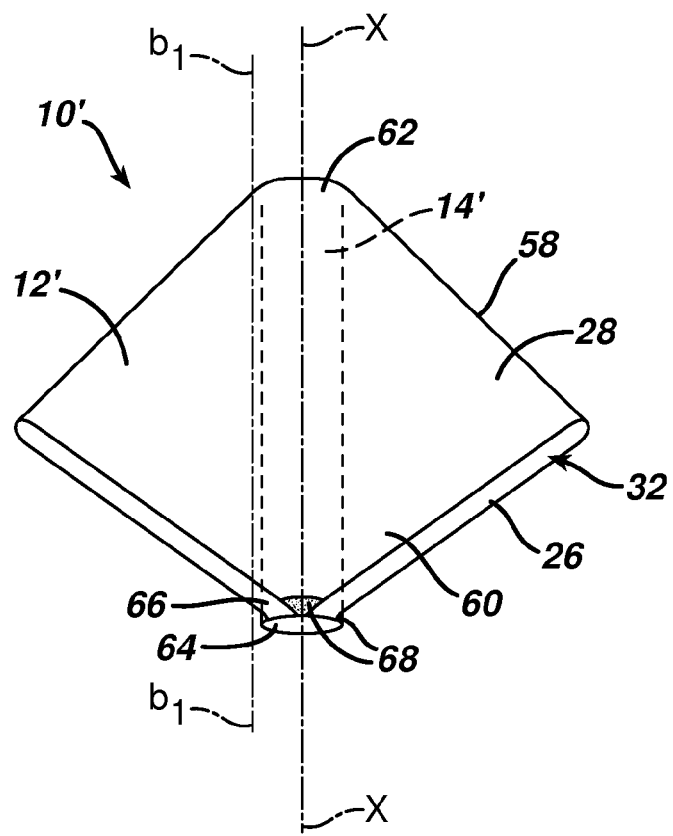
FIGS. 7a-e show various aspects and orientations of an intravaginal device of the present invention.
Figure 7B:
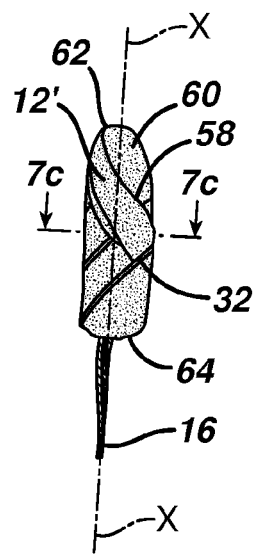
Figure 7C:
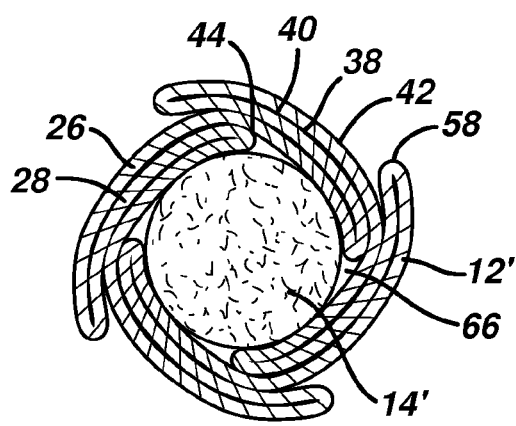
Figure 7D:
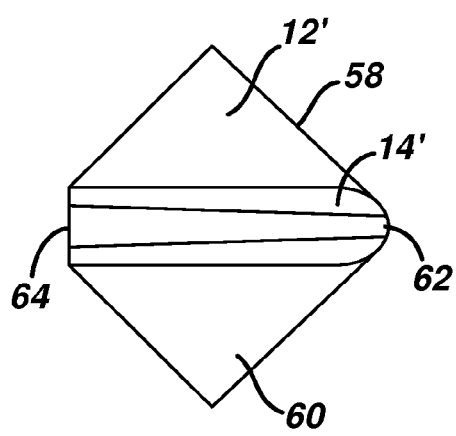
Figure 7E:
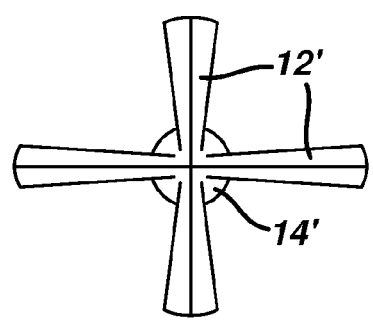

A preferred embodiment with pleats is shown in FIGS. 7a-7e, where the pleats 58 are folds in the cover material 60. The pleats 58 create plates that are bendable about an infinite number of bending axes ($b_{1-i}$-$b_{1-i}$) that are substantially parallel to the longitudinal axis (X-X) of the product, which longitudinal axis extends through the insertion end 62 and withdrawal end 64. These bending axes allow the plates to wrap around the product, either partially or completely. One such bending axis ($b_1$ $b_1$) is shown in FIG. 7b.

The fluid transport element 12' is in fluid communication with the fluid storage element 14' and directs fluid from the vagina to the storage element 14'. Generally, fluid will be directed from each fluid transport element 12' to a particular region of the fluid storage element associated with that fluid transport element. Thus, if the device has only one fluid transport element 12', the fluid will contact the fluid storage element in one interface 66.

Therefore, additional fluid transport elements 12' directing fluid to additional locations of the fluid storage element 14' will improve the efficient usage of the fluid storage element 14'. For example, two fluid transport elements 12' could be directed to opposite sides of the fluid storage element 14', as shown in FIGS. 3a-3c. Each additional fluid transport element 12' can direct fluid to additional interface locations 66 of the fluid storage element 14'. For example, four evenly spaced fluid transport elements 12' allow fluid to be directed to each quarter of the fluid storage element 14' surface as shown in FIGS. 7a-7e. Five or more elements would provide even more direct access. This can allow the fluid to contact the fluid storage element 14' uniformly and help to prevent or reduce local saturation of the fluid storage element 14'.

While the above description provides for direct fluid communication between a fluid transport element 12' and the fluid storage element 14', direct fluid contact is not necessary. There can be fluid communication through an intermediate element, such as a porous medium (e.g., a foam or fibrous structure), a hollow tube, and the like.

Enlarging the area of the interface 66 between the fluid transport element 12' and fluid storage element 14' can also help to maximize the fluid communication. For example, elongating the interface by increasing the length of the fluid transport element 12' allows more fluid to flow into the fluid storage element 14'.

The fluid transport element 12' may extend in any orientation from the surface of the fluid storage element 14'. It is not necessary for the fluid transport element to be on the surface of the fluid storage element.

Figure 8:
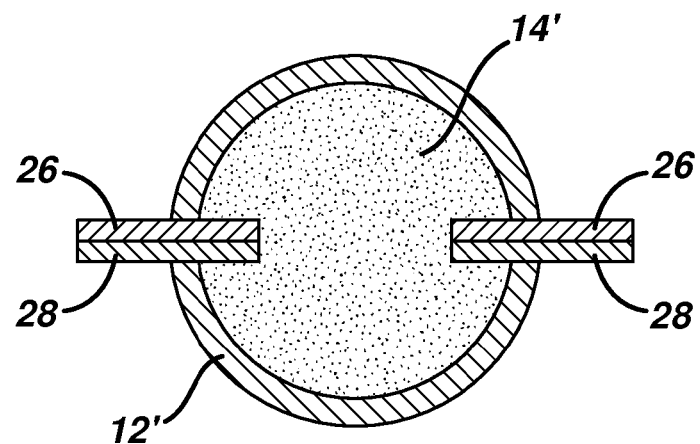
FIG. 8 shows a transverse cross-section of an alternate embodiment having a pair of fluid transport elements partially extending into the storage element.

The inter-plate capillary gap 36 formed by first and second plates 26, 28 can terminate at the interface 66 or can extend into and/or through the fluid storage element 14'. An example of the fluid transport element 12' extending into the fluid storage element 14' is shown in FIG. 8. The parallel plates can have additional layers on top of them as long as these additional layers allow fluid to enter the plates. The first and second plates may be arranged such that they can be extended in a plane that is parallel to the longitudinal axis of the device. Alternately, they may also be arranged such that they can be extended in a plane that is perpendicular to the longitudinal axis of the device, or in any orientation between these extremes (not shown).

The first and second plates 26, 28 can end at the boundary of the fluid transport element 12' or can extend into the fluid storage element 14'. FIG. 8 shows two sets of parallel plates extending into the storage element. The parallel plates can have additional layers on top of them as long as these additional layers allow fluid to enter the plates.

The fluid transport element 12' may be formed to extend from the surface of the fluid storage element 14' as in FIG. 3a-3c. In an alternative embodiment, the withdrawal string 16 could be replaced by a pair or another combination of ribbon-like parallel plates (not shown).

The fluid transport element 12' can be made in any convenient shape, including semicircular, triangular, square, hourglass etc. Additionally the two plates of the element do not have to be completely coextensive, as long as they are at least partially in a facing relationship.

The parallel plates forming the fluid transport element can be of any flexibility as long as the material is able to transport fluid to the fluid storage element while the device is in use. It is also preferable that the fluid transport element be sufficiently flexible to provide the user with comfort while inserting, wearing and removing the device.

Parallel plates can be held in close proximity to the storage element in a variety of ways including directly or indirectly via an additional element to the storage element. A variety of methods can be used to attach the fluid transport element 12' including but not limited to heat, adhesive, ultrasonics, sewing, and mechanically engaging the fluid storage element 14'. An example of a heat-sealed attachment 68 is shown in FIG. 7a.

The fluid transport element(s) 12' can be attached at the sides, insertion end 62, and/or withdrawal end 64 of the intravaginal device 10. Additionally, the fluid transport element(s) 12' may be attached to themselves and not to the storage element as in a parallel plates bag type covering of the storage element. The parallel plates could also be attached to the withdrawal string 16. Additional means of attachment are disclosed in the commonly-assigned, copending patent applications entitled. "Intravaginal Device with Fluid Acquisition Plates" (U.S. Ser. No. 60/572,054), "Intravaginal Device with Fluid Acquisition Plates and Method of Making" (U.S. Ser. No. 60/572,055), both filed on even date herewith, the contents of which are herein incorporated by reference.

Figure 9:
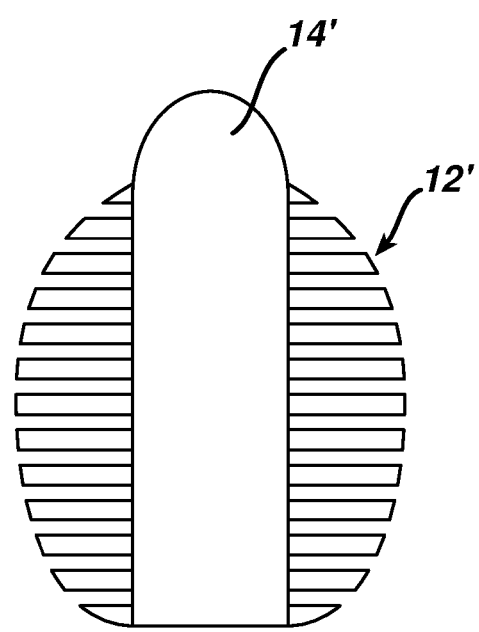
FIG. 9 shows a side view of an alternate embodiment with multiple fluid transport elements extending from the fluid storage element in planes substantially perpendicular to its longitudinal axis.

Multiple fluid transport elements can be layered on top of each other or placed next to each other. FIG. 9 shows a plurality of fluid transport elements 12' extending from the sides of the storage element 14' in a plane perpendicular to the axial direction thereof. These fluid transport elements 12' can be a variety of lengths and can be on part or the entire surface.

Figure 10:
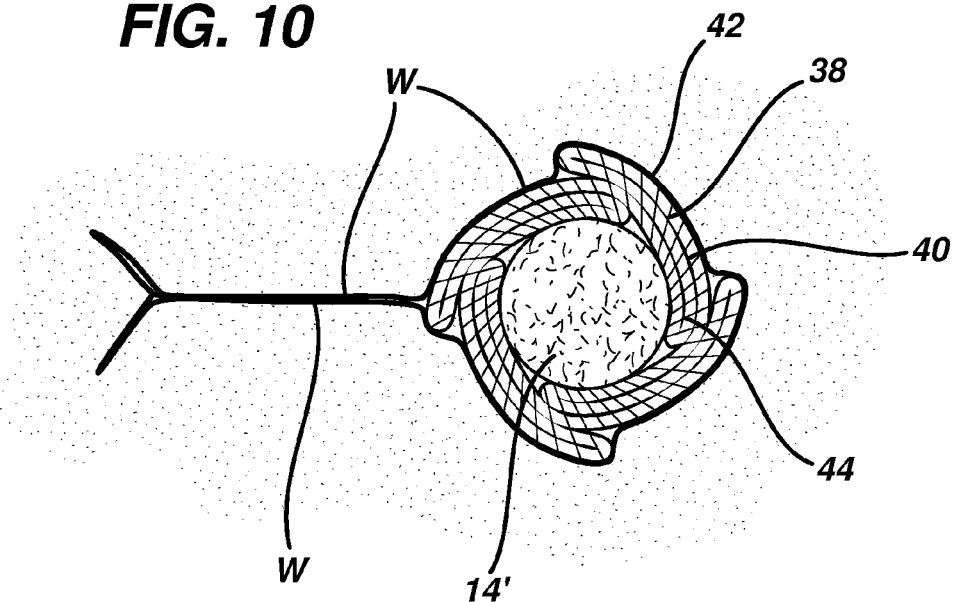
FIG. 10 shows a transverse cross-section of a human vagina with a tampon according to FIG. 7b disposed therein with the fluid transport elements remaining wrapped around the fluid storage element.

During use, fluid transport element(s) 12, 12' can take on many configurations within the vagina. For example, a fluid transport element 12" may extend into the vagina away from the fluid storage element 14", as shown in FIG. 2. Alternatively, the fluid transport element(s) 12' may remain wound about the fluid storage element 14', contacting the vaginal wall "W" only through the outwardly oriented surface 42 (FIG. 10).

Figure 11A:
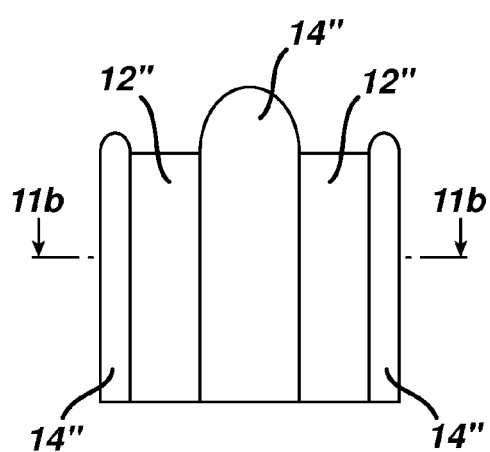
FIG. 11a shows a side elevation of an alternate embodiment of the present invention in which fluid transport elements connect a plurality of fluid storage elements.
Figure 11B:
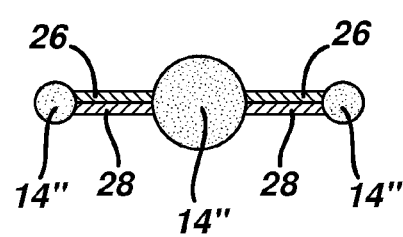
FIG. 11b shows a transverse cross-section along line 11b-11b.

The fluid storage element can be any convenient shape including cylindrical, cup like, hourglass, spherical, etc. It can be an absorbent or a fluid collection device. It can be in separate sections with the fluid transport element(s) 12' bridging or connecting the sections. FIGS. 11a and 11b shows a plurality of storage elements connected by two fluid transport elements 12'. (However, the outer storage elements should be removed before measuring the Wing Stability.)

The fluid storage element 14' can be made of any composition known in the art, such as compressed fibrous webs, rolled goods, foam etc. The storage element can be made of any material known in the art such as cotton, rayon, polyester, superabsorbent material, etc.

In one preferred embodiment, the fluid storage element 14' is an absorbent tampon 10. Absorbent tampons are usually substantially cylindrical masses of compressed absorbent material having a central axis and a radius that defines the outer circumferential surface of the tampon. Such tampons are disclosed in e.g., Haas, U.S. Pat. No. 1,926,900; Dostal, U.S. Pat. No. 3,811,445; Wolff, U.S. Pat. No. 3,422,496; Friese et al., U.S. Pat. No. 6,310,296; Leutwyler et al., U.S. Pat. No. 5,911,712, Truman, U.S. Pat. No. 3,983,875; Agyapong et al., U.S. Pat. No. 6,554,814. Tampons also usually include a cover or some other surface treatment and a withdrawal string or other removal mechanism.

Absorbent materials useful in the formation of the absorbent body include fiber, foam, superabsorbent, hydrogels, and the like. Preferred absorbent material for the present invention includes foam and fiber. Absorbent foams may include hydrophilic foams, foams that are readily wetted by aqueous fluids as well as foams in which the cell walls that form the foam themselves absorb fluid.

Fibers may be selected from cellulosic fiber, including natural fibers (such as cotton, wood pulp, jute, and the like) and synthetic fibers (such as regenerated cellulose, cellulose nitrate, cellulose acetate, rayon, polyester, polyvinyl alcohol, polyolefin, polyamine, polyamide, polyacrylonitrile, and the like).

The fluid storage element may also be in the form of a collection cup. Examples of such devices are disclosed in Zoller, U.S. Pat. No. 3,845,766 and Contente et al., U.S. Pat. No. 5,295,984. Collection devices are designed to assume a normally open, concave configuration, with an open side facing a user's cervix. The collection devices may be folded, or otherwise manipulated, to facilitate insertion into the vaginal canal A withdrawal mechanism, such as withdrawal string 16, is preferably joined to the fluid management device 10 for removal after use. The withdrawal mechanism is preferably joined to at least the fluid storage element 14, 14' and extends beyond at least its withdrawal end 64. Any of the withdrawal strings currently known in the art may be used as a suitable withdrawal mechanism, including without limitation, braided (or twisted) cord, yarn, etc. In addition, the withdrawal mechanism can take on other forms such as a ribbon, loop, tab, or the like (including combinations of currently used mechanisms and these other forms). For example, several ribbons may be twisted or braided to provide parallel plates structures.

Tampons are generally categorized in two classes: applicator tampons and digital tampons, and a certain amount of dimensional stability is useful for each type of tampon. Applicator tampons use a relatively rigid device to contain and protect the tampon prior to use. To insert the tampon into a body cavity, the applicator containing the tampon is partially inserted into the body cavity, and the tampon can be expelled from the applicator into the body cavity. In contrast, digital tampons do not have an applicator to help guide them into the body cavity and require sufficient column strength to allow insertion without using an applicator.

While the applicator tampon is protected by the rigid applicator device and the applicator tampon need not as have high a degree of column strength as a digital tampon, applicator tampons do require dimensional stability (especially radial) to be acceptable for use. This dimensional stability provides assurance, for example, that the tampon will not prematurely grow and split its packaging material or become wedged in a tampon applicator.

Figure 12:
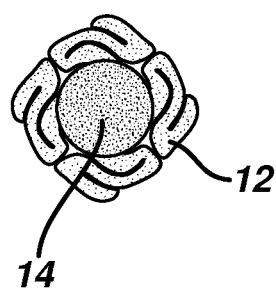
FIG. 12 shows a transverse cross-section of the present invention having a plurality of fluid transport elements folded against the fluid storage element.
Figure 13:
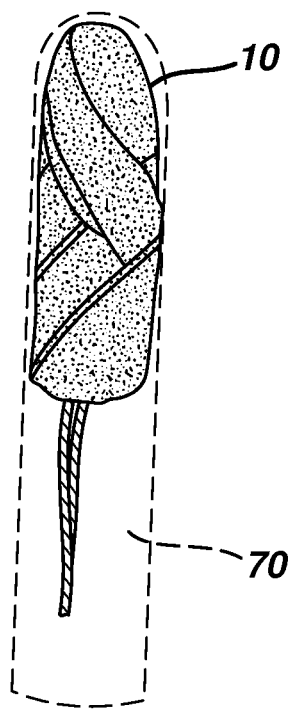
FIG. 13 shows a side elevation of a wrapped tampon within an applicator.
Figure 14A:
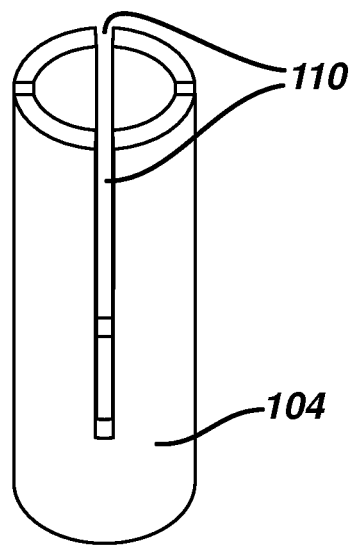
FIGS. 14a-f show a Wing Bending Test apparatus.
Figure 14B:
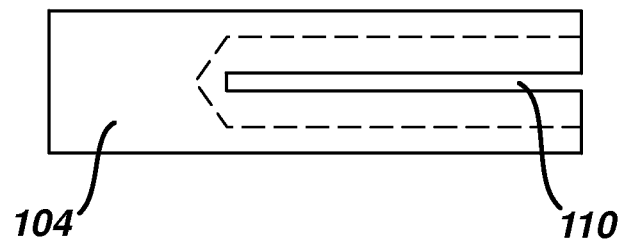
Figure 14C:
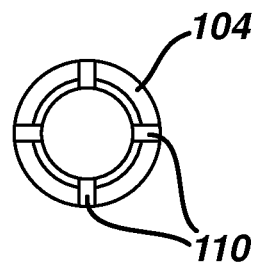
Figure 14D:
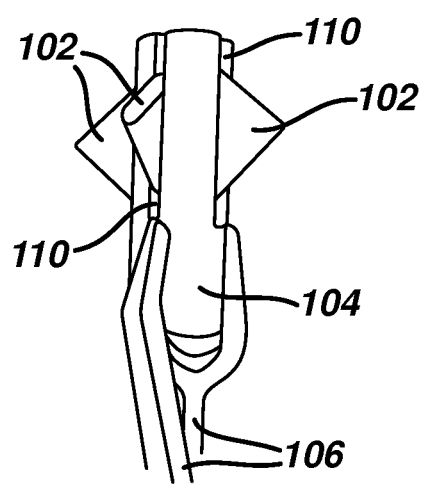
Figure 14E:
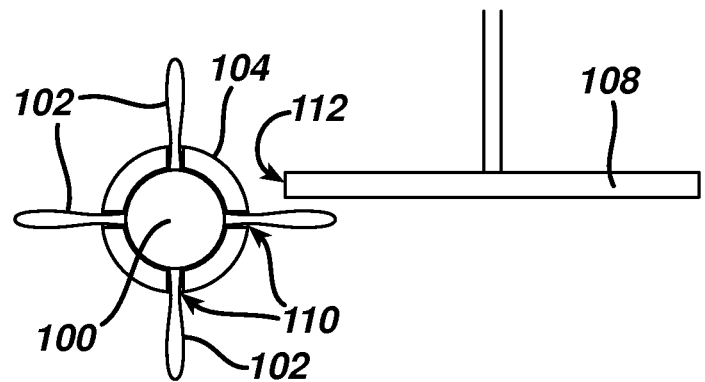
Figure 14F:
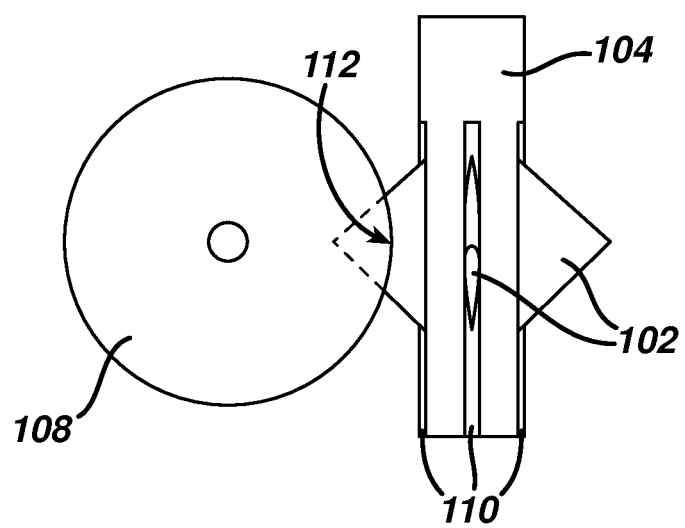

Further, the fluid management device can be collapsed for packaging and insertion. For example, at least a portion of a major surface of the fluid transport element 12', such as the outwardly oriented surface 42, may be in contact with at least a portion of an outer surface of the fluid storage element 14'. This can be achieved by wrapping the fluid transport element(s) around the fluid storage element 14' (as shown in FIG. 7b). Alternatively, the fluid transport element(s) 12' may be folded or pleated (e.g., in an accordion-like manner as shown in FIG. 12) against the fluid storage element 14'. The thus-compacted device can then be packaged, (e.g., within an applicator or alone in a wrapper). FIG. 13 shows a wrapped tampon within an applicator 70 (in phantom).

EXAMPLES

The present invention will be further understood by reference to the following specific Examples that are illustrative of the composition, form and method of producing the device of the present invention. It is to be understood that many variations of composition, form and method of producing the device would be apparent to those skilled in the art. The following Examples, wherein parts and percentages are by weight unless otherwise indicated, are only illustrative.

Several variations of the tampon generally shown in FIGS. 7a-7e were made using different fluid transport element materials (identified below) in Table 1. The wings on these tampons (Examples 1, 3-5, 7, and 8) had 2 plies. Examples 2, 6, and 9 had single ply wings formed by cutting along the edge of the wing defined by the fold in the wing material. The products were measured according to the "Wing Bending Test" (described below) to determine the Wing Stability as reported in Table 1.

TABLE 1

| Example | Material Description | # of Plies | Avg. Peak Force ($g_f$) | Min | max | Std. Dev. |
|---|---|---|---|---|---|---|
| 1 | 0.5 mil EMB 685 | 2 | 0.4 | 0.23 | 0.57 | 0.17 |
| 2 | 0.5 mil EMB 685 | 1 | 0.108 | 0.09 | 0.135 | 0.024 |
| 3 | o.b.® SilkEase film cover | 2 | 1.54 | 1.14 | 2.19 | 0.57 |
| 4 | o.b.® SilkEase film cover | 1 | 0.61 | 0.28 | 1.28 | 0.46 |
| 5 | 2 mil EMB 685 | 2 | 3.56 | 2.85 | 4.77 | 1.05 |
| 6 | 1.0 mil MYLAR "D" | 2 | 10.1 | 9.08 | 10.72 | 0.89 |
| 7 | 1.0 mil MYLAR "D" | 1 | 0.89 | 0.75 | 1.09 | 0.18 |

EMB 685 is available from Tredegar Film Products (Richmond, Va. USA). O.b.® SilkEase tampon is available from Johnson & Johnson GmbH, Dusseldorf, Germany and the apertured film cover is described in U.S. Ser. No. 09/345,090. MYLAR "D" is available from GE Polymershapes Film Business located in Devens, Mass. USA.

Figure 15:
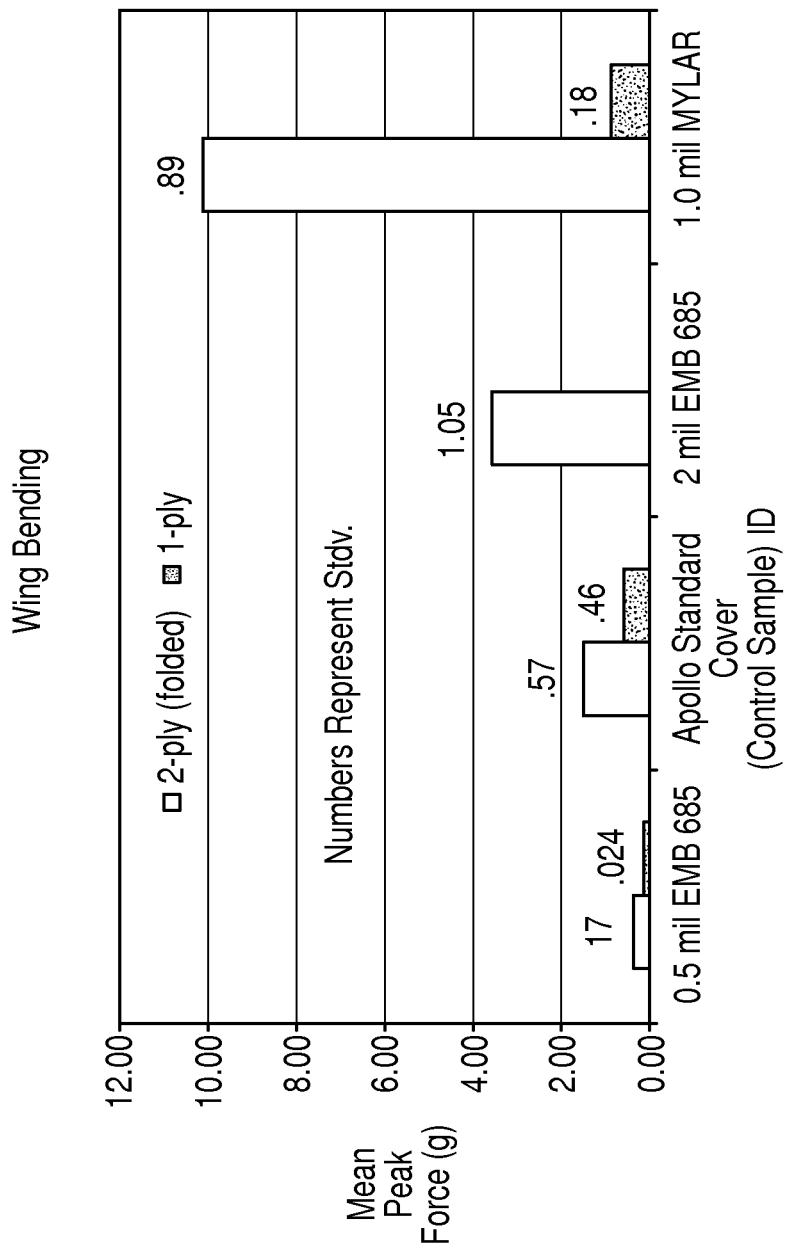
FIG. 15 is a graphical representation of data of Table 1 generated using the Wing Bending Test apparatus of FIG. 14.

The data resulting from these tests are illustrated graphically in FIG. 15. The material as configured for Example 2 was judged to be unacceptable in use and believed to collapse as shown in FIG. 4c, while the material of Example 6 was judged to be at an upper extreme of acceptable stiffness.

Wing Bending Test

One method to determine the stability of materials used in the construction of the fluid transport element is Wing Stiffness. Referring to FIG. 14a-14f, this test is carried out by placing a tampon 100 with one or more wing(s) 102 into a holding apparatus 104, and the holding apparatus 104 was fixed into a clamp 106 with one wing 102 centered under a compression disc 108. The compression disc 108 has a downward stroke of 12.7 mm, and contacts the wing 102 to bend it. The compression peak gram force is measured and recorded for a minimum of three samples.

Apparatus:
Instron machine
200 g Load cell
Compression disc (58 mm diameter)
Hollow tube with at least one slot (holding apparatus)
Stand with clamp to hold holding apparatus
Preparation:
A 200 gram load cell with 58 mm diameter compression disc was installed in an Instron Model 1125-8175 testing machine
The load cell was calibrated
Test compression speed was set to 127 mm/minute
Test stroke length was set to 19 mm Test Sample Set-Up and Procedure
Tampon 100 with wing 102 was inserted into the holding apparatus 104 with tampon base completely inside the holding apparatus 104 with the wing 102 extending out of slot 110;
The holding apparatus 104 was placed into the clamp 106 and positioned with the wing 102 centered underneath the disc 108. The outer edge 112 of the disc 108, closest to the holding apparatus 104, was adjusted to provide a 5 mm gap therebetween with the wing 102 extending beyond the gap sufficiently to maintain engagement between wing 102 and with disc 108 during test, at least until peak force is determined;
The compression disc 108 was adjusted to provide a 1-2 mm gap to the wing 102 at the start of the compression stroke
The compression stroke of the Instron Model 1125-8175 was initiated, and the compression disc 108 bends the wing 102
A minimum of three samples was tested, the peak force for each sample was recorded, and the average peak force and standard deviation were calculated The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:
1. An intravaginal device comprising:
   a. at least one fluid transport element comprising:
      i. a first plate having an outwardly oriented surface and an inwardly oriented surface;
      ii. a second plate coupled to the first plate;
         1) that has a first surface disposed and maintained in facing relationship with the inwardly oriented surface of the first plate and an opposite surface; and
         2) that is arranged and configured to separate from the first plate sufficiently to provide inter-plate capillary action; and
   b. a fluid storage element having a longitudinal axis, the fluid storage element being in fluid communication with the at least one fluid transport element
   wherein the at least one fluid transport element is arranged and configured to bend about an axis substantially parallel to the longitudinal axis of the fluid storage element, the at least one fluid transport element has a Wing Stiffness of less than about 10 $g_f$, and the at least one fluid transport element is arranged and configured to direct fluid to an associated interface with the fluid storage element.
2. The device of claim 1, wherein the at least one fluid transport element has a Wing Stiffness of about 0.4 $g_f$ to about 4 $g_f$.
3. The device of claim 2, wherein the at least one fluid transport element has a Wing Stiffness of about 0.5 $g_f$ to about 3 $g_f$.
4. The device of claim 3, wherein the at least one fluid transport element has a Wing Stiffness of about 0.5 $g_f$ to about 2 $g_f$.

* * * * *